US008759580B2

(12) United States Patent
Ernst et al.

(10) Patent No.: US 8,759,580 B2
(45) Date of Patent: Jun. 24, 2014

(54) METHOD FOR THE PRODUCTION OF AMINOALKANE ACID AMIDES

(75) Inventors: Martin Ernst, Heidelberg (DE);
Andreas Kusche, Kleinfischlingen (DE);
Gunnar Heydrich, Limburgerhof (DE);
Horst Grafmans, Bad Dürkheim (DE);
Holger Evers, Ludwigshafen (DE);
Johann-Peter Melder, Böhl-lggelheim (DE); Harald Meiβner, Hassloch (DE);
Torsten Freund, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 914 days.

(21) Appl. No.: 12/158,200

(22) PCT Filed: Dec. 15, 2006

(86) PCT No.: PCT/EP2006/069777
§ 371 (c)(1),
(2), (4) Date: Jun. 19, 2008

(87) PCT Pub. No.: WO2007/071626
PCT Pub. Date: Jun. 28, 2007

(65) Prior Publication Data
US 2008/0306299 A1 Dec. 11, 2008

(30) Foreign Application Priority Data

Dec. 20, 2005 (DE) .......................... 10 2005 060 803
Jun. 21, 2006 (EP) ..................................... 06115783

(51) Int. Cl.
C07C 231/04 (2006.01)
(52) U.S. Cl.
USPC ........................................................ 564/124
(58) Field of Classification Search
USPC ........................................................ 564/124
See application file for complete search history.

(56) References Cited

U.S. PATENT DOCUMENTS

| 3,235,576 A | 2/1966 | Chiusoli at al. |
| 3,801,610 A | 4/1974 | Werdehausen et al. |
| 3,816,483 A | 6/1974 | Werdehausen et al. |
| 4,119,665 A * | 10/1978 | Weitz et al. ............ 564/130 |
| 4,322,552 A | 3/1982 | Kleemann et al. |
| 4,780,542 A | 10/1988 | Lalezari |
| 6,331,624 B1 * | 12/2001 | Koch et al. ............ 540/538 |
| 6,525,222 B2 | 2/2003 | Nouwen et al. |
| 2003/0153749 A1 | 8/2003 | Ohlbach et al. |

FOREIGN PATENT DOCUMENTS

| DE | 597305 | | 5/1934 |
| DE | 2026832 | | 12/1971 |
| DE | 2110060 | | 9/1972 |
| DE | 2601461 A1 | | 7/1977 |
| DE | 2601462 A1 | | 7/1977 |
| DE | 2947825 A1 | | 6/1981 |
| DE | 10357978 | * | 7/2005 |
| EP | 0963975 A1 | | 12/1999 |
| EP | 1106600 A2 | | 6/2001 |
| GB | 1 564 582 | * | 4/1980 |
| JP | 10-59801 | * | 3/1998 |
| WO | WO-01/77068 A2 | | 10/2001 |
| WO | WO-01/96294 A1 | | 12/2001 |

OTHER PUBLICATIONS

Murakami et al, Bull. Chem. Soc. Japan, 64, 2744-2750, 1991.*
Thompson et al, J. Org. Chem., 46, 4907-4911, 1981.*
Schmeer et al, J. of Solution Chemistry, vol. 19, No. 12, 1990, 1175-1189.*
Hanyu et al, Tetrahedron Letters, 45(48), 8871-8874, 2004.*
Buckley et al., "Aliphatic Nitro-compounds. Part XIII. Preparation and Reduction of 2-Nitroalkyl Cyanides", *Imperial Chemical Industries Limited, Research Laboratories*, pp. 1500-1503 (1947).

* cited by examiner

*Primary Examiner* — Shailendra Kumar
(74) *Attorney, Agent, or Firm* — Drinker Biddle & Reath LLP

(57) ABSTRACT

The invention relates to a process for preparing aminoalkanamides by reacting cyanoalkanoic esters with a) ammonia or an amine and b) hydrogen in the presence of a catalyst, the reaction with component b) being started simultaneously or not later than a maximum of 100 minutes after commencement of the reaction of the cyanoalkanoic ester with component a).

22 Claims, No Drawings

METHOD FOR THE PRODUCTION OF AMINOALKANE ACID AMIDES

RELATED APPLICATIONS

This application is a national stage application (under 35 U.S.C. §371) of PCT/EP2006/069777, filed Dec. 15, 2006, which claims benefit of German application 10 2005 060 803.5, filed Dec. 20, 2005, and European application 061 157 83.0, filed Jun. 21, 2006.

The present invention relates to a process for preparing aminoalkanamides by reacting a cyanoalkanoic ester with a) ammonia or an amine and b) hydrogen in the presence of a catalyst, any intermediates occurring not being isolated and the reaction with component b) being started simultaneously or not later than a maximum of 100 minutes after commencement of the reaction of the cyanoalkanoic ester with component a).

The reaction of carboxylic acid or of a carboxylic ester with ammonia (amidation) is known in principle. For instance, DE-20 26 832 describes a process for preparing carboxamides in which straight-chain and branched, saturated and unsaturated carboxylic acids or esters thereof are reacted with ammonia in the presence of a catalyst. Suitable catalysts are compounds, soluble in the reaction mixture, of metals of groups IVb and Vb of the Periodic Table of the Elements (PTE), in particular metal compounds of titanium, zirconium and tantalum. DE-A 21 10 060 describes a corresponding process for preparing N-substituted carboxamides using primary and secondary aliphatic, cycloaliphatic or mixed aliphatic/cycloaliphatic amines instead of ammonia.

The preparation of aminoalkanamides too is already known. As early as 1934, DE-A 597 305 described the conversion of cyanoalkanamides (especially cyanoacetamide derivatives) to the corresponding aminoalkanamides by catalytic hydrogenation. The cyanoalkanamides are prepared in a preceding (separate) reaction step by reacting the corresponding cyanoalkanoyl halide with ammonia or an amine. G. D. Buckley et al. (J. Chem. Soc. 1947, pages 1500 to 1503) state that the reduction of 2-nitroalkyl cyanides with hydrogen in the presence of a catalyst (for example a Raney nickel catalyst, also referred to hereinafter as Ra—Ni, or, as a further example, palladium on calcium carbonate) gives rise to the corresponding aminoalkanamide.

An alternative process is described in U.S. Pat. No. 4,780,542, according to which an acid is first converted to an anhydride with an alkyl chloroformate in an aqueous medium and this anhydride can then be reacted with alcohol to give an ester or alternatively with an amine to give an aminoalkanamide.

The reaction of 5-cyanovaleramide with hydrogen in the presence of a catalyst to give 6-aminocapronamide is described in WO 01/77068. The starting material (5-cyanovaleramide) is in turn prepared beforehand in a separate reaction step; for example, it can be prepared by reacting the corresponding cyanovalerate with ammonia in the presence of alcohol. An analogous process is described in DE-A 29 47 825, according to which 4-aminobutyramide hydrochloride is prepared by hydrogenating 3-cyanopropionamide in the presence of a solvent inert under the reaction conditions, of a noble metal catalyst and of hydrogen chloride at a temperature between 5 and 80° C. The reactant used (3-cyanopropionamide) can be prepared from the corresponding dinitrile by partial hydrolysis.

U.S. Pat. No. 3,235,576 relates to a process for preparing ω-aminocapronamides. The starting compound used here is the methyl ester of 7-cyano-2,5-heptadienoic acid which is first reacted with ammonia to give the corresponding amide. In a first hydrogenation reaction, for example using a palladium catalyst, the corresponding 7-cyanoheptanamide is prepared and the isolated intermediate is converted in a second hydrogenation reaction using a cobalt- and nickel-containing catalyst to the corresponding ω-aminocapronamide. Alternatively, it is also possible to start from the corresponding unsaturated amide.

DE-A 26 01 462 relates to a two-stage process for preparing 6-aminocapronamide, a 5-cyanovaleric ester being reacted with excess ammonia in a first reaction stage over a period of from 2 to 6 hours and the intermediate formed being hydrogenated to 6-aminocapronamide in a second reaction stage in the presence of a cobalt- and/or nickel-containing supported catalyst. DE-A 26 01 462 does indicate that it is possible in principle to carry out the first reaction step (amidation: reaction of the ester with ammonia) actually in the presence of the catalyst required in the second reaction step (hydrogenation: conversion of the cyanoalkanamide to the aminoalkanamide) and not to isolate the intermediate formed (cyanoalkanamide). However, it cannot be discerned either from DE-A 26 01 462 or from any other prior art document that the amidation and hydrogenation of the starting material (cyanoalkanoic ester) can be carried out simultaneously, or that the hydrogenation can be carried out directly after the amidation. All relevant prior art documents state that the first reaction step (amidation) has to be carried out fully over a period of at least 2 hours, in order to hydrogenate the intermediate which forms (cyanoalkanamide) to the aminoalkanamide in a second reaction step.

In contrast, DE-A 26 01 461 relates to a process for preparing alkyl ω-aminoalkanecarboxylates, in which alkyl ω-cyanoalkanecarboxylates are hydrogenated at elevated temperature and elevated pressure using ammonia in the presence of supported nickel and/or cobalt catalysts. In this process, a hydrogenation of the cyano group to the corresponding amine thus takes place, but no amidation is carried out since the ester function of the starting substance is retained.

It is an object of the present invention to provide a novel process for preparing aminoalkanamides by reacting cyanoalkanoic esters with a) ammonia or an amine and b) hydrogen in the presence of a catalyst.

According to the invention, this object is achieved by the reaction of a cyanoalkanoic ester at elevated pressure with a) at least one molar equivalent of ammonia or one molar equivalent of amine and b) hydrogen in the presence of a catalyst, any intermediates occurring not being isolated and the reaction with component b) being started simultaneously or not later than a maximum of 100 minutes after commencement of the reaction of the cyanoalkanoic ester with component a).

The process according to the invention has the advantage that it can be carried out more rapidly compared to the processes known from the prior art. For example, no catalyst change is required for the amidation and hydrogenation; indeed, the amidation, provided that the amidation and the hydrogenation are carried out non-simultaneously and/or spatially separated, can also be effected without the presence of a catalyst.

Moreover, the process according to the invention affords the desired product (aminoalkanamide) in high selectivities, preferably of at least 95%, more preferably of at least 98%, particularly preferably of at least 99%.

In one embodiment of the present invention, the process according to the invention has the advantage that the unconverted component a) (ammonia or amine) is removed from the reaction product (aminoalkanamide) and recovered.

Especially in a continuous process, this allows valuable reactant to be recycled into the reaction circuit. In this embodiment, another advantage is that, owing to removal conditions of component a) selected with preference, the selectivity of product can be increased further.

A further advantage can be considered to be that, when a fixed bed catalyst is used for the hydrogenation (especially a fixed bed supported catalyst), the reaction product comprises only very small traces of catalyst metals, so that a final purification by crystallization is possible. In conventional processes, the catalyst has to be removed by filtration and the product purified by distillation, since metal traces present in the end product impair the product stability and the product property (possible ligand effect). In addition, the conditions required for the distillation give rise to a low product yield.

Suitable reactants are in principle all common cyanoalkanoic esters; if appropriate, it is also possible to use a mixture of two or more cyanoalkanoic esters, but preference is given to using one cyanoalkanoic ester. If appropriate, it is also possible to use compounds which have two or more cyano groups and/or two or more ester groups. However, preferred reactants have one cyano and one ester group per molecule. If appropriate, instead of the ester group, it is also possible to use the corresponding molecule having one acid group. Examples of cyanoalkanoic esters are the methyl or ethyl esters of cyanoacetic acid, cyanopropionic acid, cyanobutyric acid, cyanovaleric acid or cyanocaproic acid, the cyano group is preferably on the terminal carbon atom of the parent alkanoic acid. If appropriate, the basic alkanoic acid structure may have further substituents, preferably one or two $C_1$-$C_3$-alkyl groups, in particular two methyl substituents. Preferred cyanoalkanoic esters have, including the carbon atoms of the cyano and of the ester group, from 4 to 10 carbon atoms, the cyano function being on the terminal carbon atom of the basic alkanoic acid skeleton. Particular preference is given to methyl 2-cyano-2,2-dimethylacetate or to the corresponding ethyl ester.

The cyanoalkanoic ester is amidated with at least one molar equivalent of component a), preferably at a from 2- to 30-fold molar excess of component a), more preferably with a from 5- to 25-fold molar excess. When a plurality of ester functions in the reactant are amidated, the amount of component a) has to be increased correspondingly.

Suitable components a) are ammonia or an amine; if appropriate, it is also possible to use mixtures. However, preference is given to using only one component a), in particular ammonia. When an amine is used, suitable amines are in particular monoalkyl- or dialkylamines (to obtain the corresponding monoalkylated or dialkylated amide), in particular methylamine or dimethylamine.

In a preferred embodiment of the process according to the invention, the reactant used is methyl 2-cyano-2,2-dimethylacetate and the component a) used is ammonia.

The reactant and in particular the intermediate obtained in the amidation (cyanoalkanamide) is reacted with hydrogen (component b); hydrogenation) in the presence of a catalyst. Suitable catalysts are in principle all hydrogenation catalysts known to those skilled in the art. The catalyst may, for example, be a sponge catalyst, supported catalyst, thin-layer catalyst or unsupported catalyst, preferably a supported catalyst. The catalyst is preferably present in the form of a fixed bed catalyst, in particular in the form of a supported catalyst. Preferred catalysts comprise at least one noble metal of group VII and VIII, preferably cobalt (Co) and nickel (Ni), and also optionally at least one metal from the group of copper, manganese, chromium or iron. When a supported catalyst is used, the support may be selected from the customary metal oxides such as aluminum oxide, zirconium oxide, silicon dioxide or mixtures of these metal oxides, preference being given to aluminum oxide and zirconium oxide, particular preference to zirconium oxide. Examples of preferred catalysts are Raney cobalt catalysts (referred to hereinafter as Ra—Co) or Raney nickel catalysts—this type of catalyst is available as a commercial product in different versions under the name Raney™ cobalt or Raney™ nickel. Further examples of preferred catalysts are supported hydrogenation catalysts prepared from nickel oxide, cobalt oxide, copper oxide and zirconium oxide, which may, if appropriate, also comprise further metal components. Suitable catalysts and processes for preparing these catalysts can be taken, for example, from the documents Mozingo et al., Organic Synth. Coll. Vol. 3, pages 181 ff, Fieser and Fieser, Reagents for Org. Synth. Vol. 1, pages 723-731. EP-A 0 963 975 or EP-A 1 106 600.

The conversion of the cyanoalkanoic ester to the corresponding aminoalkanamide is carried out at elevated pressure, preferably at from 10 to 250 bar, more preferably at from 50 to 220 bar, particularly preferably at from 80 to 210 bar. If appropriate, the reaction can also be effected at standard pressure. The temperature may be between 20 and 150° C., preferably from 60 to 150° C., more preferably from 80 to 120° C., particularly preferably from 80 to 110° C.

The process according to the invention is carried out in such a way that the reaction of the reactant (cyanoalkanoic ester) with component a) and component b) is either started simultaneously or the reaction with component b) is started a maximum of 100 minutes after commencement of the reaction of the reactant with component a). Preference is given to carrying out the process according to the invention in such a way that the reaction of the reactant with component b) is started a maximum of 100 minutes after commencement of the reaction of the reactant with component a).

In the case of the second option, the reaction with component b) is thus effected after a maximum delay time of 100 minutes. Preference is given to selecting a delay time of from 5 to 100 minutes. Any intermediates which occur are not isolated. What is crucial is that component b) is not added to the reactant before the addition or the reaction of component a) with the reactant because the amidation of aminoalkanoic esters proceeds as a side reaction only in minor amounts. When the hydrogenation is not carried out simultaneously with the amidation of the cyanoalkanoic ester, it can be assumed that the intermediate formed is mainly the corresponding cyanoalkanamide.

When the hydrogenation is not started until after commencement of the amidation, the hydrogenation is more preferably from 5 to 60 minutes later than the commencement of the amidation (delay time of from 5 to 60 minutes). Particular preference is given to a delay time of from 8 to 20 minutes.

In one embodiment of the present invention, components a) and b) are fed stepwise to the reactant. In particular, this method is employed in a batch process, by stepwise feeding first of component a) and then of hydrogen in a solution of the cyanoalkanoic ester. This embodiment is used more preferably in an autoclave.

In a further alternative embodiment, in which the hydrogenation is not started until after commencement of the amidation, and which is likewise preferably employed in an autoclave, the catalyst, a solution of the cyanoalkanoic ester (reactant) and component a), and also a portion of the hydrogen, are first initially charged at a maximum pressure of 10 bar. In the course of this, a maximum temperature of 60° C. should not be exceeded; the temperature is preferably from 20 to 30° C. Subsequently, the temperature is increased to from 70 to 150° C., preferably to from 75 to a maximum of 120° C., and the hydrogen pressure is increased to from 50 to 210 bar by adding further hydrogen. The increase in the hydrogen pressure and in the temperature can be effected simultaneously or in succession. Preferably, the temperature is first increased slowly and, after the temperature has attained the desired end value (greater than 70° C.), hydrogen is injected rapidly up to the desired end pressure value (greater than 50 bar). The delay time is calculated here commencing with the combination of the reactant solution and of component a) up to the time at which the temperature is at least 70° C. and the hydrogen pressure is at least 50 bar.

Alternatively, this embodiment can also be carried out by initially charging only the solution of the reactant and component a) and the catalyst, and not adding the hydrogen until commencement of the temperature increase. The delay time is calculated in this case too commencing with the time of combination of the reactant with component a) up to the time at which the temperature is at least 70° C. and the hydrogen pressure is at least 50 bar. It is also possible to not add the hydrogen until the temperature increase is complete.

In a further embodiment of the process according to the invention, especially in a semibatchwise or continuous process, the amidation and the hydrogenation are effected with spatial separation from one another by upstream connection of a delay time zone. The delay time in the case of such a delay time zone is defined as the total volume of reactant, component a) and solvent per unit volume of the delay time zone per hour ($t=Vol_R+Vol_a+Vol_S)/Vol_{DT}/1$ hour). In this case, the appropriate reactant and component a) (preferably ammonia), each of which is fed continuously, may react as early as when they pass through a delay time zone before they reach the actual hydrogenation reactor. This delay time zone may also exist in a section of the hydrogenation reactor which is charged with material having only low catalytic activity, if any, (such as steel rings, steatite, etc.) or in which the temperature is kept below a threshold temperature needed for the hydrogenation.

When the amidation and the hydrogenation are carried out with spatial separation from one another by virtue of upstream connection of a delay time zone, the temperature in this delay time zone is from 20 to 100° C., preferably from 30 to 60° C. After passage through this delay time zone, the hydrogenation is effected at a temperature of preferably from 60 to 150° C., more preferably at from 75 to 120° C. If appropriate, the amidation and the hydrogenation may also be carried out at the same temperature in a range between 20 and 150° C.

This procedure is advantageous when the amine which is formed in the hydrogenation of the nitrile can react either intra- or intermolecularly with the reactant ester group, or when the hydrogenation is to be carried out under conditions which do not favor the amidation. The aforementioned embodiment is thus advantageous especially when relatively long-chain cyanoalkanoic esters are to be converted to the corresponding aminoalkanamide.

The process can be carried out in one step in a solvent, for example in an alcohol or N-methylpyrrolidone (NMP), preferably in a monohydric aliphatic alcohol, more preferably in an alcohol from the group of methanol (MeOH), ethanol (EtOH), propanol (PrOH), i-PrOH, 1-butanol (1-BuOH), 2-BuOH, 1-pentanol, 2-pentanol, 3-pentanol. The solvent may be used in a fraction of from 5 to 95% [% by weight] in the reaction mixture, preferably from 20 to 70%, more preferably from 30 to 60%.

As already stated above, the process can be operated in batchwise, semibatchwise or continuous mode, preference being given to the continuous reaction. The product can be isolated and purified by distillation or crystallization or a combination of the two. Preference is given to crystallization. Crystallization can be performed especially when the hydrogenation step has been carried out in the presence of a fixed bed catalyst, because the product in this case has only very small traces of the metals present in the catalyst as an impurity.

In a preferred further version of the invention, the methylcyano ester is hydrogenated as a 50% solution in 2-butanol in the presence of 7 equivalents of liquid ammonia in a batch autoclave at 100° C. over Raney nickel (5% by weight) and simultaneously converted to the amide. The catalyst is removed by filtration and the product is isolated by distillation.

One of the advantages of supported hydrogenation catalysts which are used as a fixed bed catalyst, compared with sponge catalysts, is the better resistance against washing-out of metal ions. In a particularly preferred embodiment of the process, the methylcyano ester as a 40% solution in MeOH is combined with from 10 to 25 equivalents of ammonia in a tubular reactor charged with displacement bodies (the ester being converted to the amide) and, after a delay time of from 8 to 20 minutes at from 80 to 120° C. and from 150 to 250 bar, hydrogenated over a supported hydrogenation catalyst prepared from 20% NiO, 28% CoO, 13% CuO and 31% $ZrO_2$. The product is isolated from the crude solution by one-stage crystallization.

In a further embodiment of the present invention, the unconverted component a) (i.e. the fractions of ammonia or amine which have not been reacted with cyanoalkanoic ester) is removed after the reaction with component b) (hydrogenation). Preference is given to removing the unconverted component a) at temperatures below 150° C., more preferably below 130° C., especially preferably below 110° C.

In a further embodiment of the present invention, the unconverted component a) is removed preferably at a lower temperature than the temperature in the reaction with component b) (hydrogenation). Preference is given to removing the unconverted component a) at temperatures below 150° C., more preferably below 130° C., especially preferably below 110° C.

It is also preferred when the removal step as such (the removal of the unconverted component a) from the reaction mixture) is performed as rapidly as possible. In the context of the present invention, the expression "as rapidly as possible" shall be understood to mean that the removal step as such lasts for a maximum of 300 minutes, more preferably for a maximum of 200 minutes, especially preferably for a maximum of 120 minutes.

Preference is given to removing unconverted component a) both at relatively low temperature and as rapidly as possible.

In a further embodiment, especially in a continuous process, unconverted component a) is removed in a separate apparatus. Separate apparatus shall be understood to mean all removal units known to the person skilled in the art, especially a pressurized gas column or a distillation column. This means that the reaction mixture comprising the product (aminoalkanamide), unconverted component a) and, if appropriate, a solvent are transferred from the apparatus in which the hydrogenation is performed to the removal unit by methods known to those skilled in the art.

The unconverted component a) is removed from the removal unit preferably at temperatures below 150° C., more preferably below 130° C., especially preferably below 110° C. The residence time of the aminoalkanamide (product) in the removal of the unconverted component a) in the removal unit is preferably from 1 to 300 minutes, more preferably from 1 to 200 minutes, especially preferably from 1 to 120 minutes.

The removal of unconverted component a) as rapidly as possible from the reaction mixture has been found to be advantageous especially because the amidation is an equilibrium reaction which can be shifted in the direction of the ester when the amine or the ammonia is removed from the reaction mixture continuously at elevated temperature, and sufficient time is given for the relatively slow reaction.

In the workup of the aminoalkanamide present, for example, in an alcoholic solution, back-reaction to give the corresponding ester of the alcohol present in the reaction mixture or of the alcohols can therefore occur when the ammonia or the amine used is removed from the mixture at elevated temperature. It is therefore important to keep the temperature in the removal as low as possible and/or to minimize the residence time of the aminoalkanamide (product) in the removal unit (for example a pressurized gas column or a distillation column).

The invention will be illustrated with reference to the examples which follow:

EXAMPLES

Autoclave Experiments

General

The reactant and the catalyst are initially charged in the autoclave and the contents are inertized by purging with nitrogen. Subsequently, 5 bar of hydrogen are injected. The desired amount of ammonia is metered in and then the autoclave is heated slowly with stirring to the reaction temperature (80° C.). This step takes an average of 90 min, i.e. the delay time of the reactant solution in contact with ammonia is approx. 90 min. On attainment of the reaction temperature, hydrogen is injected rapidly to the pressure specified in Table 1 below and consumed hydrogen is replaced by metering under pressure control over the experiment time until no further hydrogen absorption is recorded.

The autoclave experiments are carried out in a 2.5 l autoclave with hollow-shaft disk stirrer (stirrer speed approx. 600 rpm), electrical heating and jacket air cooling, 2 baffles, sparging through the autoclave lid and introduction of the hydrogen via the hollow-shaft stirrer. The weights for Raney catalysts are corrected for 10% water moisture, i.e., in real terms, 10% more water-moist catalyst is weighed out than specified. Reaction effluents are analyzed via gas chromatography (GC) (conditions: 60 m DB1701; internal diameter 0.32 mm; film thickness 0.25 μm; detector: FID; temperature program: 80° C.→10 K/min→280° C., 40 min, split ratio 100:1, carrier gas helium) and the compositions are reported in % by weight.

The reactor yield is determined by means of gas chromatography with internal standard (I.S.) (I.S. piperidine; the concentration thus obtained in the crude effluent is multiplied by the total mass of the crude effluent and the yield thus calculated is compared to the theoretical yield). The reactions are all carried out with methyl 2-cyano-2,2-dimethylacetate with a purity of >99.8%. The main product obtained is aminopivalinamide (3-amino-2,2-dimethylpropionamide).

TABLE 1

| Example | Pressure/bar | Catalyst | % by weight of catalyst | Solvent | Concentration % | NH$_3$/nitrile | Purity (crude, GC) % | Conversion % | Reactor yield % |
|---|---|---|---|---|---|---|---|---|---|
| 1 | 200 | Ra—Ni | 10 | NMP | 30 | 20:1 | 98.7 | 100 | not determined |
| 2 | 65 | Ra—Co | 10 | BuOH | 40 | 7.7:1 | 98.8 | 100 | 94.0% |
| 3 | 65 | Ra—Ni | 10 | BuOH | 40 | 7.7:1 | 98.2 | 99.7 | 90.6% |
| 4 | 65 | Ra—Ni | 2.5 | BuOH | 40 | 3:1 | 93.7 | 99.7 | 84.9% |
| 5 | 65 | Ra0Co | 2.5 | BuOH | 40 | 3:1 | 94.9 | 99.9 | 86.7 |
| 6 | 65 | Ra—Co | 5 | MeOH | 40 | 3:1 | 96.5 | 99.1 | 90.4 |
| 7 | 65 | Ra—Co | 5 | MeOH | 40 | 3:1 | 96.6 | 99.1 | 91.1 |
| 8 | 65 | Ra—Co | 5 | BuOH | 40 | 3:1 | 90.0 | 99.4 | 88.2 |

The examples show that very good selectivities of at least 90% are achievable with Raney nickel and Raney cobalt. The higher the amount of ammonia, the higher the catalyst concentration and the higher the hydrogen pressure, the better is the selectivity. In example 8, a metal determination is carried out, 430 ppm of Co are found in the reaction effluent.

Continuous Experiments

General

The experiment examples are carried out in a 1 l reactor (10×2000 mm), equipped with feed pumps for solvent, ammonia and nitrile ester, charged with 250 ml of steel rings in the lower and upper reactor section, and centrally with 500 ml of tablets (5×3 mm) of a hydrogenation catalyst of the following composition: 28% NiO, 28% CoO, 13% CuO and 31% ZrO$_2$, in liquid phase mode. The reduction procedure of the catalyst is as follows: the reactor is heated to 180° C. at a hydrogen feed of 50 l/h within 5 hours, then kept at 180° C. with 50 l/h of hydrogen for 20 hours, cooled under hydrogen and purged with MeOH, before ammonia and reactant and also solvent are fed in. The steel rings in the lower part of the reactor serve as the delay time zone for the amidation. 11 equivalents of hydrogen are fed in per nitrile used. The delay time is thus approx. 10 minutes.

Example 9

503 g/h of MeOH and, as the nitrile ester, methyl 2-cyano-2,2-dimethylacetate (in a weight ratio of 1:1) and 670 g of ammonia (20 equivalents of ammonia based on nitrile ester) are conducted through the reactor at 200 bar and 100° C. The volume space velocity is 0.5 kg/l*h. The effluent analysis shows (calculated without solvent) 99.89% aminopivalinamide, 0.03% methyl aminopivalate and 0.08% others. The delay time is approx. 9.8 minutes.

Example 10

250 g/h of tetrahydrofuran (THF) and methyl 2-cyano-2,2-dimethylacetate as the nitrile ester (in a weight ratio of 70:30) and 205 g of ammonia (20 equivalents of ammonia based on nitrite ester) are conducted through the reactor at 200 bar and 100° C. The volume space velocity is 0.15 kg/l*h. The effluent analysis shows (calculated without solvent) 33.083% aminopivalinamide, 65.68% methyl aminopivalate and 0.49% others. The delay time is approx. 27 minutes.

As can be seen, it is possible to almost fully amidate the nitrile ester (0.03% methyl aminopivalate remain) in MeOH as an example of a monohydric aliphatic alcohol, even at a very high volume space velocity (based on the nitrile ester without solvent) of 0.5 kg/l*h in the embodiment in which the amidation and the hydrogenation of the reactant take place simultaneously, while the amidation proceeds more slowly in THF. Even at a low volume space velocity of 0.15 kg/l/h, approx. 34% of the nitrile ester is nevertheless still amidated, so as to result in a mixture of approx. 66% of the aminopivalic ester with the aminopivalinamide. The former is no longer converted to amide under the reaction conditions.

What is claimed is:

1. A process for preparing aminoalkanamides comprising reacting a cyanoalkanoic ester at elevated pressure with a) at least one molar equivalent of ammonia or one molar equivalent of amine and b) hydrogen in the presence of a catalyst, wherein any intermediates formed are not isolated, wherein the reaction with b) is commenced simultaneously with or not later than a maximum of 100 minutes after commencing the reaction of said cyanoalkanoic ester with a), and wherein said cyanoalkanoic ester is methyl 2-cyano-2,2-dimethylacetate or ethyl 2-cyano-2,2-dimethylacetate.

2. The process of claim 1, wherein the reaction of said cyanoalkanoic ester with a) and b) is commenced simultaneously.

3. The process of claim 1, wherein said cyanoalkanoic ester is first reacted with a) and the intermediate formed thereby is reacted directly with b).

4. The process of claim 3, wherein the reaction is carried out by stepwise addition of a) and b).

5. The process of claim 4, wherein said catalyst and a solution of said cyanoalkanoic ester and a) are initially charged at a temperature of 60° C. or less, followed by addition of hydrogen, increasing the pressure to a pressure in the range of from 80 to 210 bar, and increasing the temperature to a temperature in the range of from 80 to 150° C.

6. The process of claim 5, wherein a portion of said hydrogen is initially charged at a pressure of 10 bar or less.

7. The process of claim 3, wherein the reaction of said cyanoalkanoic ester with a) and b) takes place with spatial separation from one another by virtue of upstream connection of a delay time zone.

8. The process of claim 7, wherein the temperature in said delay time zone is in the range of from 20° C. to 100° C. and the temperature in the hydrogenation is in the range of from 60° C. to 150° C.

9. The process of claim 1, wherein said cyanoalkanoic ester is methyl 2-cyano-2,2-dimethylacetate.

10. The process of claim 1, wherein a) is ammonia.

11. The process of claim 1, wherein said catalyst is a fixed bed catalyst.

12. The process of claim 1, wherein said catalyst comprises nickel, cobalt, copper, and/or zirconium.

13. The process of claim 1, wherein the reaction is carried out in the presence of a solvent.

14. The process of claim 1, wherein the reaction with b) is started after a time delay of from 8 to 20 minutes.

15. The process of claim 1, further comprising purifying the aminoalkanamide obtained by crystallization.

16. The process of claim 1, wherein unconverted a) is removed at a temperature below 130° C. after the reaction with b).

17. The process of claim 1, wherein unconverted a) is removed after the reaction with b), said removal being effected at a temperature lower than the temperature of the reaction with b) or said removal step is performed as rapidly as possible.

18. The process of claim 17, wherein said removal is effected at a temperature below 110° C. or said removal is performed within 120 minutes or less.

19. The process of claim 16, wherein said removal is effected in a separate apparatus.

20. The process of claim 19, wherein the residence time of the aminoalkanamide during said removal of a) in said separate apparatus is in the range of from 1 to 120 minutes.

21. The process of claim 13, wherein said solvent is a monohydric aliphatic alcohol.

22. The process of claim 19, wherein said separate apparatus is a pressurized gas column or a distillation column.

* * * * *